United States Patent
Sharma et al.

(10) Patent No.: US 10,809,341 B1
(45) Date of Patent: Oct. 20, 2020

(54) READOUT-SEGMENTED ECHO PLANAR IMAGING WITH K-SPACE AVERAGING

(71) Applicant: CANON MEDICAL SYSTEMS CORPORATION, Otawara-shi (JP)

(72) Inventors: Anuj Sharma, Hudson, OH (US); Andrew J. Wheaton, Shaker Heights, OH (US)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 16/389,394

(22) Filed: Apr. 19, 2019

(51) Int. Cl.
*G01R 33/567* (2006.01)
*G01R 33/561* (2006.01)
*G01R 33/48* (2006.01)
*A61B 5/055* (2006.01)

(52) U.S. Cl.
CPC .......... *G01R 33/5676* (2013.01); *A61B 5/055* (2013.01); *G01R 33/4818* (2013.01); *G01R 33/5615* (2013.01)

(58) Field of Classification Search
CPC ............ G01R 33/5676; G01R 33/5615; G01R 33/4818; A61B 5/055
See application file for complete search history.

(56) References Cited

U.S. PATENT DOCUMENTS

| | | | | |
|---|---|---|---|---|
| 5,581,184 A * | 12/1996 | Heid ................. | G01R 33/56554 | 324/309 |
| 6,118,273 A * | 9/2000 | Takizawa ......... | G01R 33/56554 | 324/309 |
| 6,541,970 B1 * | 4/2003 | Takizawa ......... | G01R 33/56554 | 324/309 |
| 6,703,834 B2 * | 3/2004 | Ikezaki ............ | G01R 33/56554 | 324/307 |
| 2002/0002331 A1 | 1/2002 | Cline et al. | | |
| 2005/0218893 A1 * | 10/2005 | Kumai ............... | G01R 33/5616 | 324/309 |

(Continued)

OTHER PUBLICATIONS

David A. Porter, et al., "High Resolution Diffusion-Weighted Imaging Using Readout-Segmented Echo-Planar Imaging, Parallel Imaging and a Two-Dimensional Navigator-Based Reacquisition", Magnetic Resonance in Medicine, vol. 62, 2009, pp. 468-475.

(Continued)

*Primary Examiner* — G.M. A Hyder

(74) *Attorney, Agent, or Firm* — Oblon, McClelland, Maier & Neustadt, LLP

(57) ABSTRACT

An apparatus and method are provided to correct motion artifacts in magnetic resonance imaging (MRI) data by obtaining magnetic resonance imaging (MRI) data, the MRI data including imaging segments and corresponding navigator segments, each imaging segment sampled over a respective regions of two or more regions of a k-space grid, one of the navigator segments being selected as a reference navigator segment; generating, for each imaging segment of the imaging segments, a respective phase map based on the reference navigator segment and a corresponding navigator segment of the each imaging segment; applying the respective phase maps to the corresponding imaging segments to generate corrected imaging segments; averaging the corrected imaging segments in k-space to generate averaged imaging segments; and reconstructing an MRI image based on the averaged imaging segments.

17 Claims, 5 Drawing Sheets

(56) References Cited

U.S. PATENT DOCUMENTS

| | | | | |
|---|---|---|---|---|
| 2005/0237057 A1* | 10/2005 | Porter | ............. | G01R 33/56341 |
| | | | | 324/307 |
| 2007/0236217 A1* | 10/2007 | Porter | ............... | G01R 33/5618 |
| | | | | 324/307 |
| 2012/0013336 A1* | 1/2012 | Hetzer | ................ | G01R 33/485 |
| | | | | 324/309 |
| 2012/0112745 A1* | 5/2012 | Takizawa | .......... | G01R 33/4824 |
| | | | | 324/309 |
| 2012/0286777 A1* | 11/2012 | Frost | ............... | G01R 33/56341 |
| | | | | 324/307 |
| 2013/0033262 A1* | 2/2013 | Porter | ............. | G01R 33/56341 |
| | | | | 324/309 |
| 2013/0307542 A1* | 11/2013 | Chen | ..................... | G01R 33/32 |
| | | | | 324/318 |

OTHER PUBLICATIONS

Wenchuan Wu, et al., "Image Formation in Diffusion MRI: A Review of Recent Technical Devlopments", J. Magn. Reson. Imaging, vol. 46, No. 3, Sep. 2017, pp. 646-662.

Samantha J. Holdsworth, et al., "Robust GRAPPA-Accelerated Diffusion-Weighted Readout-Segmented (RS)-EPI", Magnetic Resonance in Medicine, vol. 62, 2009, pp. 1629-1640.

* cited by examiner

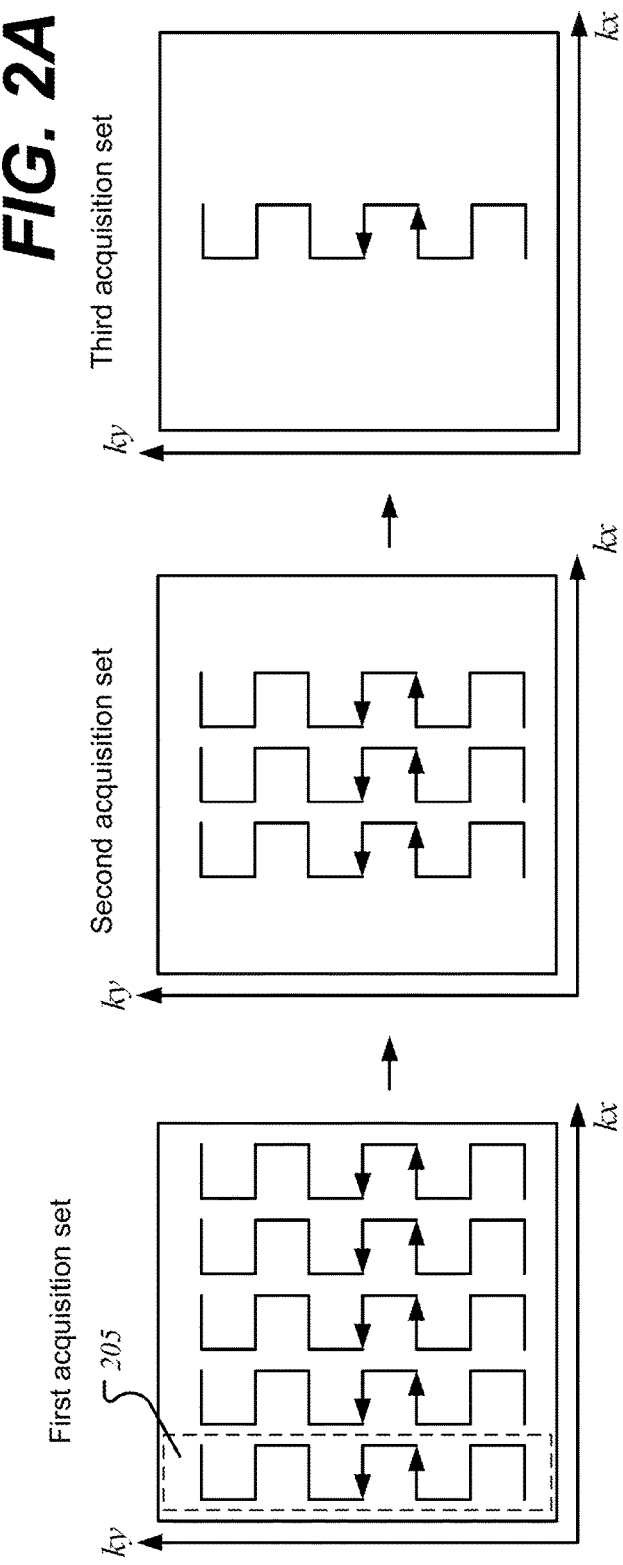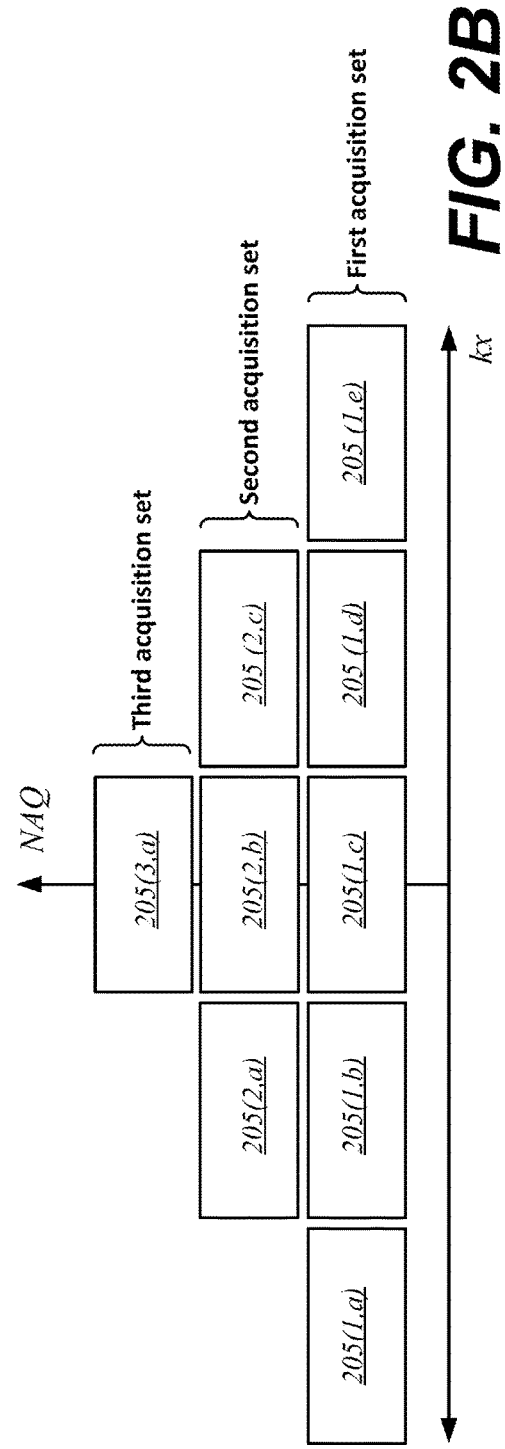

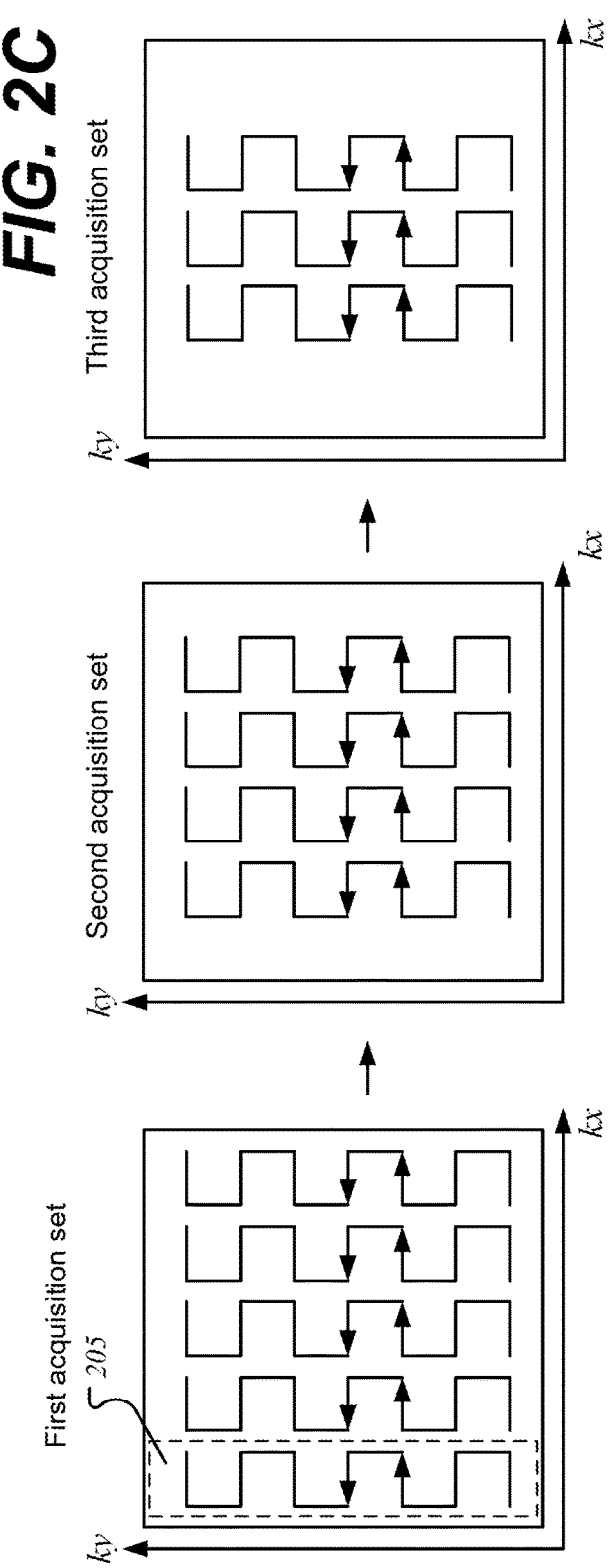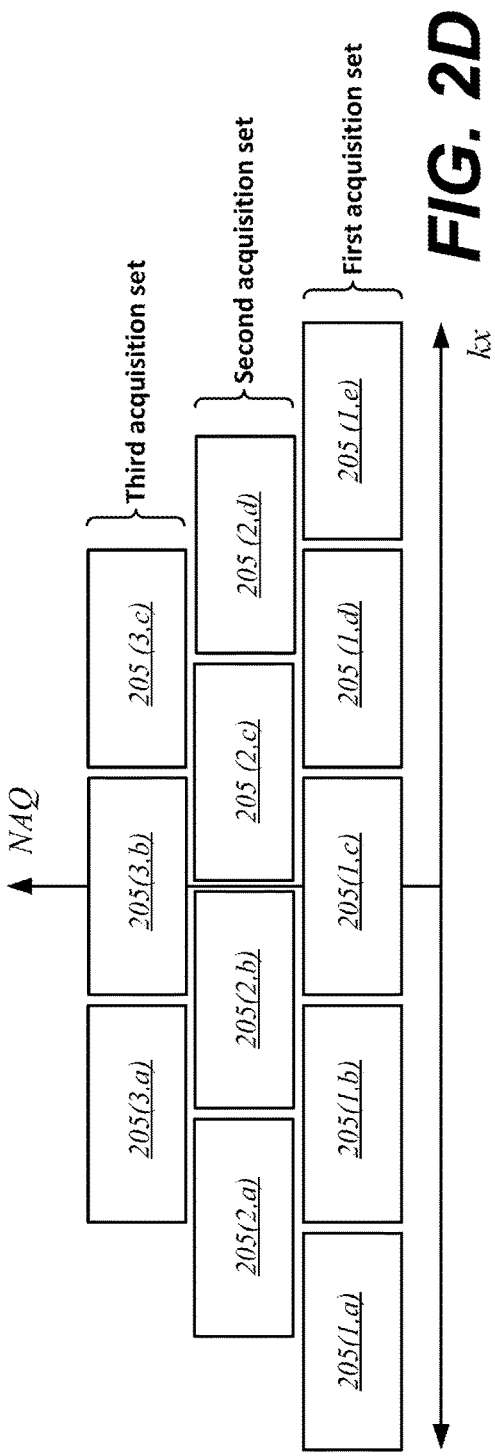

READOUT-SEGMENTED ECHO PLANAR IMAGING WITH K-SPACE AVERAGING

FIELD

This disclosure relates to correcting motion artifacts in magnetic resonance imaging (MRI), and, more particularly, to using readout-segmented echo planar imaging (RSEPI) with joint navigator correction to perform averaging in the k-space domain.

BACKGROUND

The background description provided herein is for the purpose of generally presenting the context of the disclosure. Work of the presently named inventors, to the extent the work is described in this background section, as well as aspects of the description that cannot otherwise qualify as prior art at the time of filing, are neither expressly nor impliedly admitted as prior art against the present disclosure.

The image quality obtained during magnetic resonance imaging (MRI) is adversely affected by movements of a patient/subject, resulting in motion artifacts. This problem arises frequently due to the prolonged time required for common MRI sequences to collect sufficient data to form an image. This imaging time is commonly longer than the timescale of most types of physiological motion, including involuntary movements, cardiac and respiratory motion, gastrointestinal peristalsis, vessel pulsation, and blood and CSF flow. Examples of motion artifacts include blurring and ghosting in the image.

Echo-planar imaging (EPI) is a fast MR imaging method which allows the acquisition of full k-space in a single shot (SSEPI), for example in the time frame of 50-100 ms, thus minimizing the effects of patient motion. Following a spin-preparation, a strong switched frequency-encoding gradient may be applied simultaneously with an intermittently "blipped" low-magnitude phase-encoding gradient. Gradient echoes (GREs) may be collected with each oscillation of the readout (frequency) gradient. The end result may be a "zig-zag" traversal of k-space. EPI is the preferred readout method for time-consuming exams such as diffusion-weighted (DWI) and functional (fMRI) imaging. SSEPI has the advantage of speed but suffers from susceptibility artifacts/distortions, low signal-to-noise, and spatial blurring.

To improve image quality (IQ) while increasing scan duration, readout-segmented EPI (RSEPI) may be utilized. In RSEPI, a full acquisition of k-space data may be acquired in multiple adjacent readout (RO) segments. The k-space from each segment are combined to create a full set of k-space suitable for image reconstruction. RSEPI may additionally introduce motion artifacts due to inconsistencies between the RO segments, but this may be mitigated via navigator data (segments) acquired during the second and subsequent echoes. However, navigator data may only be consistent and compared within each acquisition set, thus rendering data across all acquisition sets disparate.

Accordingly, better methods are desired to reconstruct high-quality images from MRI data using RSEPI with joint navigator correction and imaging data (segments) averaging in k-space.

BRIEF DESCRIPTION OF THE DRAWINGS

A more complete understanding of this disclosure is provided by reference to the following detailed description when considered in connection with the accompanying drawings, wherein:

FIG. 2A illustrates a schematic block diagram for acquiring MRI data using readout-segmented echo planar imaging (RSEPI), according to an exemplary implementation of the present disclosure;

FIG. 2B illustrates a schematic block diagram of shots acquired in varying acquisition sets using non-uniform k-space averaging with RSEPI, according to an exemplary implementation of the present disclosure;

FIG. 2C illustrates a schematic block diagram for acquiring MRI data using RSEPI with offset k-space acquisition sets, according to an exemplary implementation of the present disclosure;

FIG. 2D illustrates a schematic block diagram of shots acquired in varying acquisition sets using non-uniform k-space averaging with RSEPI with offset k-space acquisition sets, according to an exemplary implementation of the present disclosure;

DETAILED DESCRIPTION

Figure 1A:
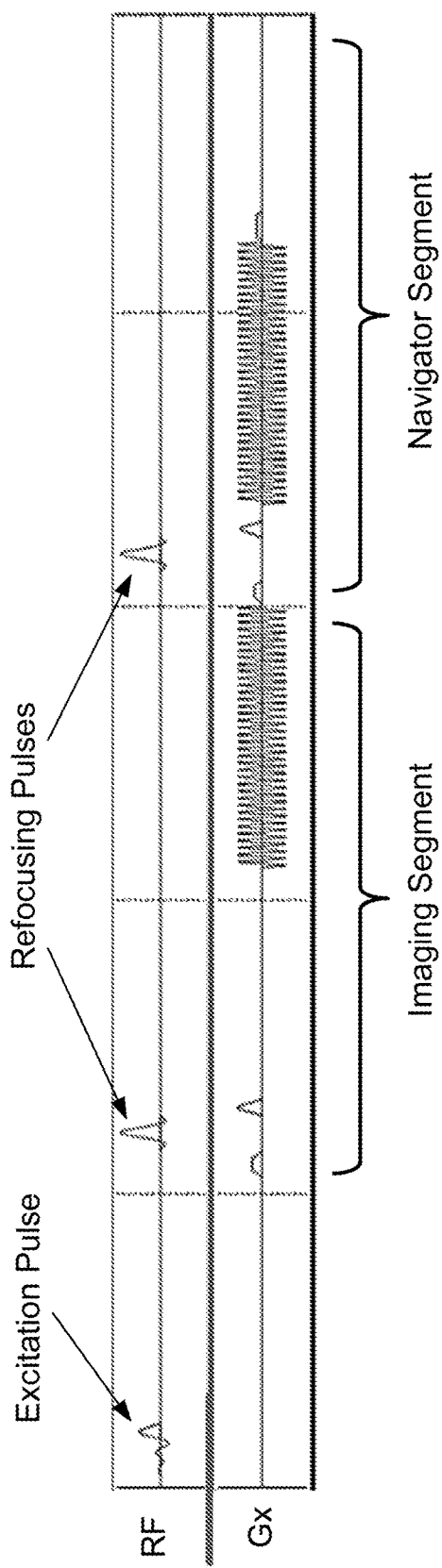
FIG. 1A illustrates a schematic of the spin echo RSEPI radio frequency (RF) pulse sequence diagram, according to an exemplary implementation of the present disclosure.

Exemplary embodiments are illustrated in the referenced figures of the drawings. It is intended that the embodiments and figures disclosed herein are to be considered illustrative rather than restrictive. No limitation on the scope of the technology and of the claims that follow is to be imputed to the examples shown in the drawings and discussed herein.

The embodiments are mainly described in terms of particular processes and systems provided in particular implementations. However, the processes and systems will operate effectively in other implementations. Phrases such as 'an embodiment', 'one embodiment', and 'another embodiment' can refer to the same or different embodiments. The embodiments will be described with respect to methods and compositions having certain components. However, the methods and compositions can include more or less components than those shown, and variations in the arrangement and type of the components can be made without departing from the scope of the present disclosure.

The exemplary embodiments are described in the context of methods having certain steps. However, the methods and compositions operate effectively with additional steps and steps in different orders that are not inconsistent with the exemplary embodiments. Thus, the present disclosure is not intended to be limited to the embodiments shown, but is to be accorded the widest scope consistent with the principles and features described herein and as limited only by the appended claims.

Furthermore, where a range of values is provided, it is to be understood that each intervening value between an upper and lower limit of the range—and any other stated or intervening value in that stated range—is encompassed within the disclosure. Where the stated range includes upper and lower limits, ranges excluding either of those limits are also included. Unless expressly stated, the terms used herein are intended to have the plain and ordinary meaning as understood by those of ordinary skill in the art. Any definitions are intended to aid the reader in understanding the present disclosure, but are not intended to vary or otherwise limit the meaning of such terms unless specifically indicated.

Motion from a patient/object during an MRI scan can introduce artifacts in reconstructed images (blurring, ghosting, signal loss, etc.), leading to misdiagnosis or requiring multiple scans to mitigate said motion errors. While some motion can be prevented, involuntary movements from the patient, such as swallowing, breathing, pulsatile flow, etc. can still occur and degrade the quality of the results. This is especially common for pediatric and geriatric patients who dislike remaining in the instrument, cannot hold their breath for long periods of time, etc.

In MRI, the data acquisition can be performed using pulse sequences that sample an object in spatial frequency space and then applying a Fourier transformation to transform the sampled echoes into the image domain, rather than sampling directly in image space. Motion artifacts can materialize in a scan due to myriad factors including the image structure, type of motion, MR pulse sequence settings, and k-space acquisition strategy. The center of k-space contains low spatial frequency information correlated to objects with large-dimension spatial features and smooth intensity variations, whereas the periphery of k-space contains high spatial frequency information correlated to edges, details, and sharp transitions. A majority of biological samples show very local spectral density in k-space centered around k=0. The kx and ky axes of k-space correspond to the horizontal (x-) and vertical (y-) axes of a two-dimensional (2D) image. The k-axes, however, represent spatial frequencies in the x- and y-directions rather than positions. Since the object in k-space is described by global planar waves, each point in k-space contains spatial frequency and phase information about every pixel in the final image. Conversely, each pixel in the image maps to every point in k-space. Simple reconstruction using an inverse FFT (iFFT) assumes the object has remained stationary during the time the k-space data were sampled. Therefore, errors from object motion have a pronounced effect on the final reconstructed image because a change in a single sample in k-space can affect the entire image. Since scan durations can take minutes in order to acquire the data necessary for image reconstruction, attempts have been made to accelerate the imaging speed as well as detect and correct for motion in images.

As previously mentioned, EPI may be utilized to fully sample k-space in a single shot in a short time frame on the scale of 50-100 ms. In EPI, phase encoding (PE) k-space velocity, also known as the k-velocity, is determined via Δky/ETS, wherein Δky is the k-space distance between two consecutive PE lines and ETS is echo train-spacing which is the time between any two successive echoes. The k-velocity can be increased by increasing Δky or reducing ETS. However, large increases in Δky can lead to significant residual aliasing artifacts even after a parallel imaging reconstruction. And reduction in ETS leads to increased slew rate which is limited by the gradient amplifier and patient peripheral nerve stimulation safety specifications. Thus, k-velocity cannot be increased beyond a certain practical limit. This k-velocity limit is the source of two major disadvantages of EPI: image distortion and low spatial resolution. Since the amount of distortion is inversely proportional to k-velocity, the lower k-velocity in EPI leads to significant image distortions. On the other hand, for a fixed slew rate, readout (RO) resolution may be increased by increasing the ETS but this may result in lower k-velocity and increased distortion. Conversely, for a fixed ETS, slew rate can be increased to increase resolution but only to a certain extent due to the gradient hardware and patient safety limits.

To increase RO resolution and reduce distortion, Readout-Segmented EPI (RSEPI) may be utilized at the cost of increased scan duration. K-space sampling may occur in a predetermined number of shots, for example 3-7 shots, to sample a predetermined number of k-space segments, for example 3-7 segments. Each shot may have limited transversal of k-space in the readout (kx) direction, but full resolution along the phase-encode (ky) direction. The kx coverage can be increased by acquiring more RO segments, thus increasing RO image resolution without changing ETS or slew rate. Adding more segments does not change k-velocity, so distortion remains the same, independent of the RO image resolution. By using narrow segments, for example segments with 32-64 RO points, short ETS of 300-400 μs can be achieved. This increases k-velocity, thereby resulting in lower distortion in the phase encode direction.

Referring now to the drawings, wherein like reference numerals designate identical or corresponding parts throughout the several views, FIG. 1 shows a non-limiting example of a pulse sequence applied to acquire one imaging segment together with a navigator segment to mitigate motion artifacts by correcting for phase differences between the respective imaging segments due to motion. Motion between segments may result in substantial artifacts. For example, phase mismatch between the RO segments stemming from motion can cause image artifacts such as blurring and ghosting. Therefore, each imaging segment can be accompanied by a respective navigator segment, such that phase differences between the imaging segments can be measured and corrected by comparing the respective navigator segments. For example, even though respective imaging segments can sample different regions in k-space, each of the navigator segments can be acquired at the k-space center, allowing for direct comparison and monitoring changes over time (e.g., phase differences due to motion). That is, at k-space center, the navigator segments may be repeatedly acquired to account for shot-dependent nonlinear phase differences that arise from non-rigid motion of the head or other imaged body part. As described herein, corresponding navigator segments may be acquired for all respective imaging segments and jointly phase corrected, allowing for imaging segment averaging across all acquisitions to form one set of k-space data that may be utilized for final image reconstruction.

FIG. 1A shows an RSEPI pulse sequence diagram illustrating the excitation and refocusing radio-frequency pulses in the top row and the readout gradient waveforms (Gx) in the bottom row. For simplicity, the phase-encode gradient blips and slice-direction gradient waveforms are not shown. The RF pulse sequence begins with an excitation pulse followed by two or more refocusing pulses. The first refocusing pulse generates a spin echo signal for the main image and the second refocusing pulse generates the navigator spin echo signal, both of which are measured by receive RF coils.

Figure 1B:
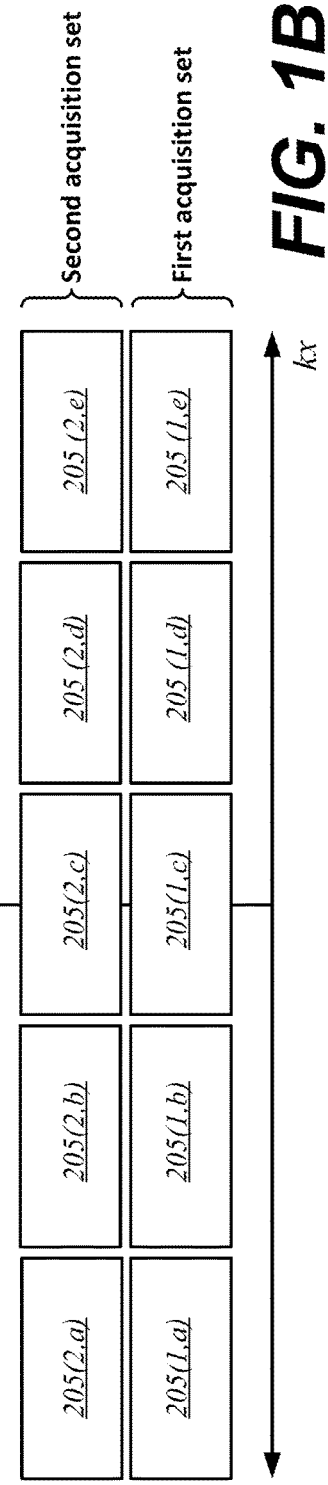
FIG. 1B illustrates a schematic block diagram of shots acquired in varying acquisition sets using uniform k-space averaging.

FIG. 1B shows a non-limiting example of shots acquired in varying acquisition sets using uniform k-space averaging. A k-space grid may be segmented into a predetermined number of segments 205(1,a-e), for example five segments (as shown). Five shots in a first acquisition set may fully sample the k-space grid across the five segments 205(1,a-e). In a second acquisition set, five additional shots may be acquired to sample the k-space grid again across the five segments 205(2,a-e) at the same locations (i.e. segments 205(1,a-e)) as acquired in the first acquisition set. In a non-limiting example, the segments 205(1,a-e), 205(2,a-e) in each acquisition set may be converted to the image domain and reconstructed to form an image, for example via an inverse Fourier Transform, and averaged in the image domain. That is, segments 205(1,a-e) from the first acquisition set may be reconstructed to produce a first image, and separately, segments 205(2,a-e) from the second acquisition set may be reconstructed to produce a second image. Subsequently, the first and second image may be averaged to produce an averaged image. Notably, all the segments 205 from any of the acquisitions sets may be rejected if the error for one of the navigator segments in the acquisition set exceeds a predetermined quality threshold. For example, if the navigator segment from the middle segment 205(1,c) in the first acquisition set is determined to exceed the predetermined quality threshold, the five segments 205(1,a-e) may be rejected and not used to reconstruct the first image. Thus, the second image may not be averaged with the first image and SNR may be decreased.

FIG. 2A illustrates a technique for acquiring MRI data using RSEPI, according to an exemplary implementation of the present disclosure. As previously described, two spin echoes may be used to acquire imaging and navigator data, also known as imaging segments and navigator segments, over the k-space grid, wherein the navigator segments may be repeatedly acquired at a central segment 205 of the k-space grid with each imaging segment to account for shot-dependent nonlinear phase differences. A first echo may be used to generate the imaging segments and a second echo may be used to generate the navigator segments. In one implementation, the k-space grid is segmented into the predetermined number of segments 205, for example five segments (as shown in the left k-space grid). A full scan of the k-space grid via RSEPI uses a predetermined number of shots, for example five shots, wherein each shot samples one of the five segments 205. Each shot is offset along the kx direction via a variable amplitude pre-phasing pulse in order to sample subsequent segments 205. The second echo is used to generate the navigator segments which sample a central segment 205 with respect to the kx direction with each shot. Although each shot may partially transverse the k-space grid in the kx direction, each shot fully traverses the ky direction. Imaging segment phase errors that arise from motion and eddy currents during the presence of large diffusion-encoding gradients may lead to shifts of k-space along both kx and ky dimensions, which can lead to gaps between adjacent segments 205 in the final assembled k-space. To include a safety margin, scan time may be traded for increased robustness against motion by partially overlapping adjacent segments 205.

Even with single-shot EPI, DWI and fMRI exams may be several minutes long. RSEPI may further increase the scan time, wherein the scan time is a linear product of the single-shot EPI scan time and the number of segments 205. For example, if five segments 205 are acquired, the scan time may increase five-fold as compared to SSEPI. Moreover, the scan time may increase when averaging of all the shots in an acquisition set, as well as when scanning additional acquisition sets. For example, as illustrated in FIG. 1B, the five segments 205 may be acquired again with an additional five shots, and the five shots may be averaged, resulting in a ten-fold scan time increase as compared to one acquisition set using SSEPI. For a given object that is being imaged, the dominant (and most clinically significant) features might be expressed in the low-frequency components. Accordingly, rather than uniformly sampling all regions of k-space, better image quality and performance might be achieved by acquiring more samples (i.e., segments) at low-frequency regions of k-space than at high-frequency regions of k-space. That is, the shots sampling the peripheral segments 205(1,a), 205(1,e) (high frequencies) of the k-space grid may acquire less information. Therefore, a non-uniform k-space sampling method may select a predetermined location for additional acquired shots in additional acquisition sets to improve image quality with a limited increase in the scan time.

In one implementation, which is illustrated in FIG. 2A, the five shots in the first acquisition set may fully sample the k-space grid across the five segments 205(1,a-e) (as shown in the left k-space grid). In the second acquisition set, fewer than five shots may be acquired to partially sample the k-space grid. For example, three shots may be acquired to sample the three more centrally disposed segments 205(2,a-c) in the k-space grid (as shown in the middle k-space grid). In a third acquisition set, fewer than five shots may be acquired to partially sample the k-space grid. For example, one shot may be acquired to sample the single substantially centered segment 205(3,a) in the k-space grid (as shown in the right k-space grid).

FIG. 2B illustrates a schematic of shots acquired in varying acquisition sets using non-uniform k-space averaging with RSEPI, according to an exemplary implementation of the present disclosure. The vertical axis may describe a number of averaging acquisitions (NAQs) acquired for segments 205 over the k-space grid, and the horizontal axis may describe the range of kx within the k-space grid that are sampled by a given imaging segment 205. As described in the previous example, segments 205(1,a), 205(1,e) on the periphery of the k-space grid may have one NAQ each, while the second inner-most segments 205(1,b), 205(2,a) on the left and right 205(1,d), 205(2,c) may have two NAQs each, and the most central segment 205(1,c), 205(2,b), 205(3,a) may have three NAQs. Therefore, in this non-uniform pattern of sampling the k-space grid, the peripheral portion of the k-space grid describing high spatial-frequency content has fewer samples than k-space regions corresponding to lower-spatial frequency content. That is, the central portion of the k-space grid describing low spatial-frequency content is sampled more frequently, than the peripheral portion.

In a scenario where the total NAQs are limited to a fixed quantity (e.g., the MRI scan is time constrained), the non-uniform pattern of sampling may provide benefit in targeting the central, low spatial-frequency content more, whereas uniformly sampling over the entire k-space grid (i.e. five segments evenly across the k-space grid in each acquisition set) would devote a greater time and resources to sampling the less information rich, peripheral portion of k-space. In a scenario where the total scan time is limited, the non-uniform pattern of sampling may provide benefit in skipping shots that may sample the segments 205(1,a), 205(1,e) on the periphery of the k-space grid in order to acquire more shots of the central segments 205(1,c), 205(2,b), 205(3,a).

While a specific example has been provided, it may be appreciated by those in the art that other non-uniform sampling patterns may be implemented. In general, the k-space grid may include N segments 205 to cover the k-space grid and the N segments 205 may be sampled with M acquisitions, wherein M≥N. The k-space grid may be divided into a plurality of portions P, wherein each portion may comprise one or more segments 205. For example, as shown in FIGS. 2A and 2B, the k-space grid may be divided into 5 portions, wherein each portion comprises one segment 205. In another non-limiting example, the k-space grid may be divided into 3 portions, wherein the left-most and right-most (the peripheral) segments 205 comprise respective portions, and the middle three segments 205 comprise an additional single portion. In this non-limiting example, the middle portion comprising the middle three segments 205 may include more low spatial-frequency content and it may be desirable to acquire more acquisitions in the middle portion. Thus, for some portions P, there may exist more than one acquisition at that portion, wherein P S N.

Due to changes (e.g., motion) between the shots, each shot acquired using RSEPI may require a correction (e.g., a phase correction due to motion) prior to averaging in k-space as compared to other EPI-based methods using image-domain averaging.

Figure 3:
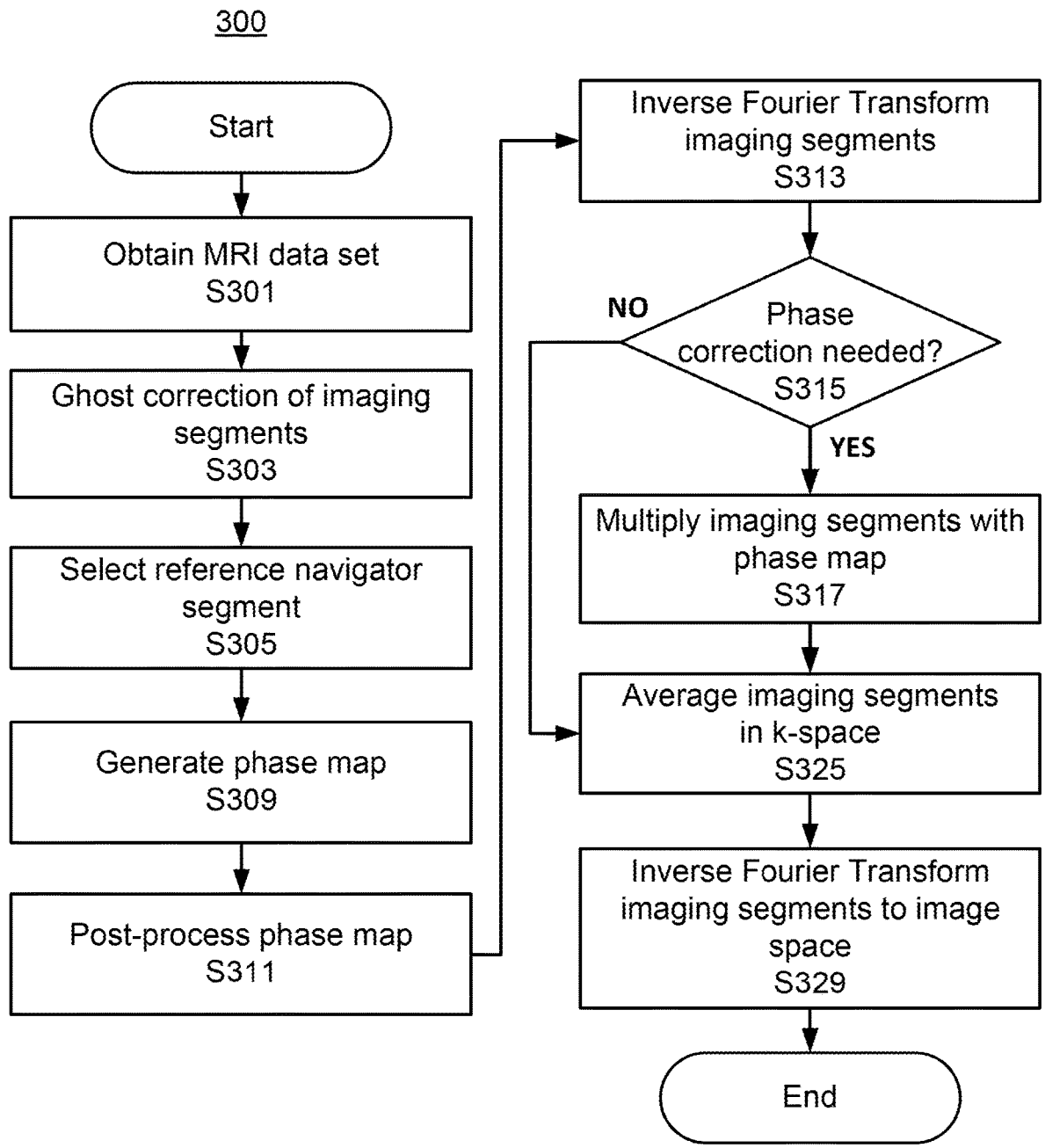
FIG. 3 illustrates a flow diagram of a method for joint navigator segment correction and averaging imaging segments in k-space, according to an exemplary implementation of the present disclosure.

FIG. 3 illustrates a flow chart for joint navigator segment correction and averaging imaging segments in k-space, according to an exemplary implementation of the present disclosure. In one implementation, the imaging segments may be averaged in k-space.

In step S301, MRI data may be acquired including imaging segments with corresponding navigator segments.

In step S303, a first correction of the imaging segments may be applied, for example a ghost correction. After this step, the navigator segment acquired with each imaging segment acquisition may be used to correct a phase difference of each of the imaging segments within each acquisition set. However, correction of imaging segments across more than one acquisition set may not be possible if the navigator segments acquired in respective acquisition sets are independently corrected and not corrected with respect to a reference across all acquisition sets.

In step S305, after all acquisitions sets have been acquired, a reference navigator segment may be selected from all the acquired navigator segments. The navigator segments may then be corrected with respect to the reference navigator segment.

In step S309, respective phase maps are generated for the imaging segments based on differences between the reference navigator and the navigator corresponding to a respective imaging segment. For example, the navigator segments and the reference navigator segment may be inverse Fourier Transformed to generate navigator images and a reference navigator image. Each of the navigator segment images may be multiplied with a conjugate of the reference navigator segment image to generate a phase map, for example a 2D phase map for a sampled 2D k-space grid.

In step S311, optional post processing, such as smoothing, may be applied to the phase map.

In step S313, the imaging segments may be inverse Fourier Transformed to generate imaging segment images.

In step S315, it is determined whether or not phase correction is needed. For example, if no motion has occurred and the phase map represents a phase correction of zero, then no phase correction is needed. In this case, method 300 can skip step S317 and proceed directly to step S325. If on the other hand a phase correction is needed, then, in step S317, the imaging segments may be multiplied with the phase map generated in step S309. The determination of whether or not phase correction is needed can proceed on an imaging segment by imaging segment basis. The phase correction may be insufficient in correcting the error due to motion, for example if the user exhibits a large motion of a body part, in which case a usability threshold may be determined for each of the imaging segments after phase correction. If the imaging segment does not meet the usability threshold, the imaging segment may be rejected.

In step S325, for the imaging segments meeting the usability threshold, the imaging segments are averaged in the k-space domain. For example, the imaging segments that did not need phase correction plus the imaging segments that were phase corrected in step S317 may be Fourier Transformed to k-space to generate corrected imaging segments. Then these corrected imaging segments can be averaged in the k-space domain to generate averaged imaging segments. The averaged imaging segments may be mapped (e.g., interpolated) onto a common grid in k-space.

In step S329, the averaged imaging segments may be inverse Fourier Transformed to generate an MRI image. To generate the MRI image, the one or more MRI system 100 can perform a reconstruction process on the scan data.

Notably, the joint navigator segment correction enables the aforementioned method to perform averaging in the k-space domain, as opposed to averaging in the image domain. In turn, this averaging in the k-space domain allows for a non-uniform distribution of imaging segments within k-space to obtain more samples in those regions of k-space that are deemed to have greater impact on the image quality. In contrast, averaging in the image domain generally requires a uniform distribution of imaging segments within k-space because, typically, each unique image that is being averaged in the image domain is generated from a unique set of imaging segments spanning the k-space domain. Further, the above-described joint navigator segment correction method enables the non-uniform distribution of imaging segments within k-space because all the acquisition sets are corrected via a common reference navigator segment. Additionally, since most of the MR signal is concentrated near the center of the k-space grid, the signal-to-noise ratio (SNR) of the non-uniform sampling pattern may closely match the SNR of a uniform sampling pattern, while preserving or reducing the total scan time.

In one implementation, the non-uniform sampling pattern with joint navigator correction may allow for selective data rejection from scans while preserving scan time. In the presence of bulk or large pulsatile motion, imaging segments and corresponding navigator segments may experience significant signal loss and become unusable. In one method, the navigator segments from an acquisition set may be reconstructed and analyzed inline during a scan to determine if the error for each navigator segment in the acquisition set exceeds a predetermined quality threshold. For example, the predetermined quality threshold may be determined via the navigator segment phase or k-space entropy. Upon determining that acquired MRI data is unusable, a user may perform a repeated acquisition of an entire acquisition set again. This may require a predetermined feedback mechanism. This may also increase scan time when repeated acquisition scans must be performed. In another method without the feedback mechanism, the user may define a predetermined number of acquisitions sets to acquire with uniform k-space sampling of the k-space grid. The navigator segments may be acquired with the corresponding imaging segments and compared after the scan has terminated. In this method, upon determining that acquired MRI data is unusable, an entire acquisition set may be rejected.

For example, two acquisition sets uniformly sampling the k-space grid including five segments 205 may be acquired (as shown in FIG. 1B), resulting in a total of ten acquired segments, with each segment 205 having two NAQs. Upon determining that one of the imaging segments in one of the two acquisitions sets, for example the middle segment 205(1,c) in the first acquisition set, includes corrupted, unusable data via comparing the corresponding navigator segment, the data in all five segments 205(1,a-e) may be rejected and excluded from averaging and final image reconstruction, thus reducing the SNR Using the non-uniform k-space sampling pattern with joint navigator segment correction of the present disclosure, the example sampling pattern in FIG. 2A and FIG. 2B may be considered, wherein the segments 205(1,a), 205(1,e) on the periphery of the k-space grid may have one NAQ each, while the second inner-most segments 205(1,b), 205(2,a) on the left and right 205(1,d), 205(2,c) may have two NAQs each, and the most central segment 205(1,c), 205(2,b), 205(3,a) may have three NAQs. As mentioned, the corresponding navigator segment to each respective imaging segment may be corrected with respect to the selected reference navigator segment, thus enabling averaging across all imaging segments.

Upon determining that the navigator segment for one of the imaging segments exceeds a predetermined error threshold, the data from that specific segment 205 may be rejected without rejecting all the data in the respective acquisition set. For example, in FIG. 2B, the middle segment 205(2,b) in the second acquisition set may be corrupted and rejected. Advantageously, the two other segments 205(2,a), 205(2,c) in the second acquisition set may still be used in averaging and final image reconstruction with all the other segments 205.

Notably, as described in this particular example, the uniform k-space sampling with disjointed navigator segment correction (FIG. 1B) results in rejection of five segments 205(1,a-e) out of ten acquired segments 205, while the disclosed method of non-uniform k-space sampling with joint navigator segment correction advantageously results in rejection of only one segment 205(2,b) out of nine acquired segments 205, while having the same or shorter total scan time. By intelligently designing the non-uniform k-space sampling pattern, this may result in simultaneously higher image quality with k-space averaging and data rejection without a feedback mechanism.

As previously mentioned, in practice, the segments 205 may be overlapped by a small fraction to avoid discontinuities in k-space, especially for data points sampled on the gradient ramps. However, even with overlapping segments 205, k-space discontinuities may occur due to errors in gradient calibration, which may be mitigated via increasing the overlap factor further. Increase in overlap factor increases the scan time by increasing the number of segments 205 required to cover the k-space grid.

FIG. 2C illustrates acquiring MRI data using RSEPI with offset k-space acquisition sets and FIG. 2D illustrates shots acquired in varying acquisition sets using non-uniform k-space averaging with RSEPI with offset k-space acquisition sets, according to an exemplary implementation of the present disclosure.

In one implementation, the disclosed method may reduce scan time by reducing or eliminating the partial overlap of adjacent segments 205. Instead, the segments 205 acquired in consecutive acquisition sets may be shifted in the kx direction such that the segments 205 overlap any two imaging segments previously adjacently sampled. Since all the navigator segments may be jointly corrected, the segments 205 may be directly averaged in k-space to mitigate k-space discontinuities. Note in FIG. 2D that each of the segments 205(2,a-d) in the second acquisition set substantially overlaps two segments 205 adjacently sampled in the first acquisition set. It may be appreciated by those in the art that the previous examples, such as those discussed in FIG. 2A, FIG. 2B, FIG. 2C, and FIG. 2D, are depicted as sampling a 2D k-space grid.

RS-ESPI may utilize precise and accurate control of the applied gradients. There may be potential secondary costs related to the gradient control necessary to achieve precise kx sampling. Namely, eddy currents may distort the kx trajectory and thus the kx samples may not be sampled at the target location. This may introduce ringing artifacts, for example. Therefore, advantageously, sampling the same kx point with several different overlapping segments 205 allows for averaging out the error in the kx trajectory introduced by any one segment 205.

Figure 4:
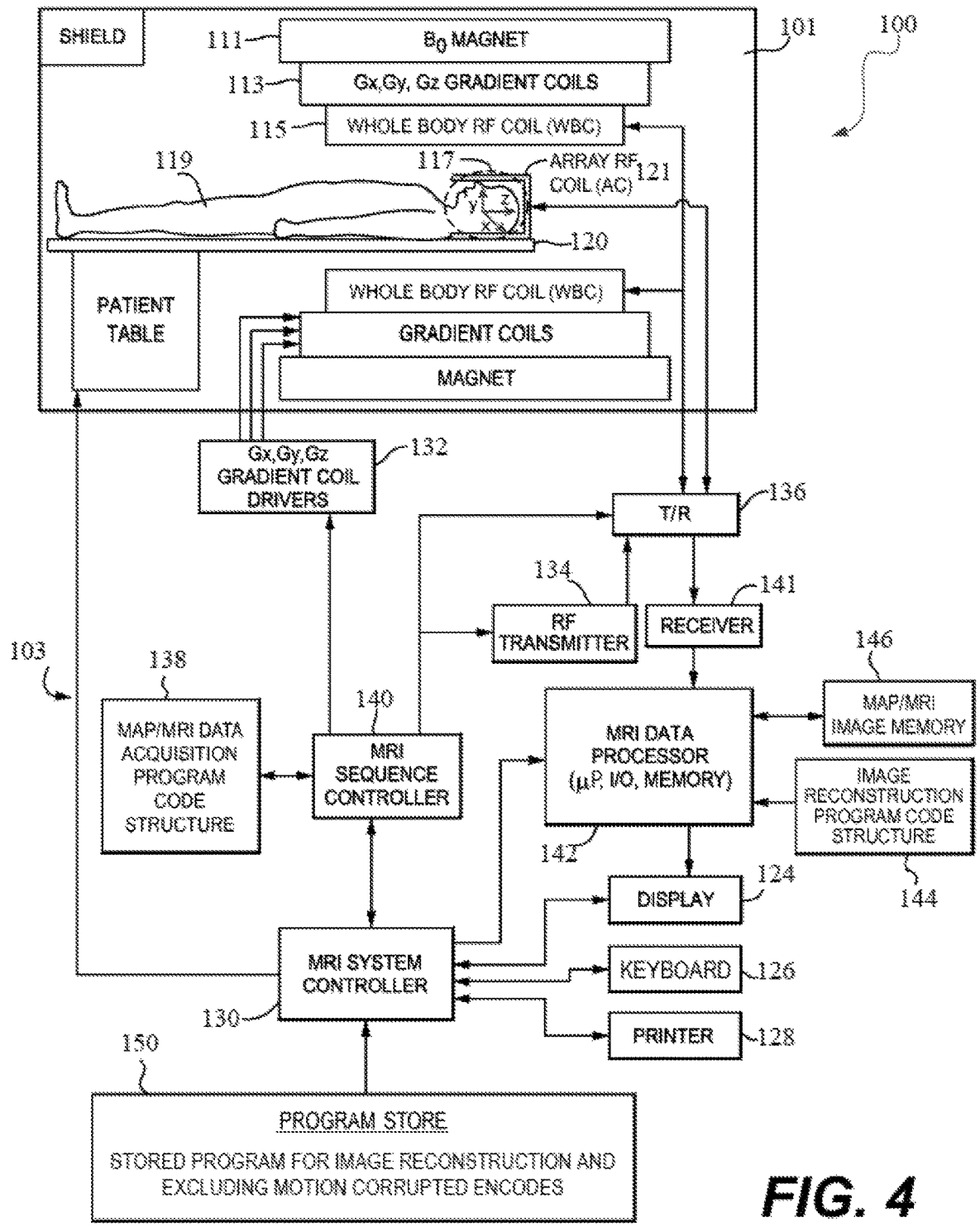
FIG. 4 illustrates a schematic block diagram of a magnetic resonance imaging (MRI) system, according to an exemplary implementation of the present disclosure.

FIG. 4 shows a non-limiting example of a magnetic resonance imaging (MRI) system 100. The MRI system 100 depicted in FIG. 4 includes a gantry 101 (shown in a schematic cross-section) and various related system components 103 interfaced therewith. At least the gantry 101 is typically located in a shielded room. The MRI system geometry depicted in FIG. 4 includes a substantially coaxial cylindrical arrangement of the static field $B_0$ magnet 111, a Gx, Gy, and Gz gradient coil set 113, and a large whole-body RF coil (WBC) assembly 115. Along a horizontal axis of this cylindrical array of elements is an imaging volume 117 shown as substantially encompassing the head of a patient 119 supported by a patient table 120.

One or more smaller array RF coils 121 can be more closely coupled to the patient's head (referred to herein, for example, as "scanned object" or "object") in imaging volume 117. As those in the art will appreciate, compared to the WBC (whole-body coil), relatively small coils and/or arrays, such as surface coils or the like, are often customized for particular body parts (e.g., arms, shoulders, elbows, wrists, knees, legs, chest, spine, etc.). Such smaller RF coils are referred to herein as array coils (AC) or phased-array coils (PAC). These can include at least one coil configured to transmit RF signals into the imaging volume, and a plurality of receiver coils configured to receive RF signals from an object, such as the patient's head, in the imaging volume.

The MRI system 100 includes a MRI system controller 130 that has input/output ports connected to a display 124, a keyboard 126, and a printer 128. As will be appreciated, the display 124 can be of the touch-screen variety so that it provides control inputs as well. A mouse or other I/O device(s) can also be provided.

The MRI system controller 130 interfaces with a MRI sequence controller 140, which, in turn, controls the Gx, Gy, and Gz gradient coil drivers 132, as well as the RF transmitter 134, and the transmit/receive switch 136 (if the same RF coil is used for both transmission and reception). The MRI sequence controller 140 includes suitable program code structure 138 for implementing MRI imaging (also known as nuclear magnetic resonance, or NMR, imaging) techniques including parallel imaging. MRI sequence controller 140 can be configured for MR imaging with or without parallel imaging. Moreover, the MRI sequence controller 140 can facilitate one or more preparation scan (pre-scan) sequences, and a scan sequence to obtain a main scan magnetic resonance (MR) image (referred to as a diagnostic image). MR data from pre-scans can be used, for example, to determine sensitivity maps for RF coils 115 and/or 121 (sometimes referred to as coil sensitivity maps or spatial sensitivity maps), and to determine unfolding maps for parallel imaging.

The MRI system components 103 include an RF receiver 141 providing input to data processor 142 so as to create processed image data, which is sent to display 124. The MRI data processor 142 is also configured to access previously generated MR data, images, and/or maps, such as, for example, coil sensitivity maps, parallel image unfolding maps, distortion maps and/or system configuration parameters 146, and MRI image reconstruction program code structures 144 and 150.

In one embodiment, the MRI data processor 142 includes processing circuitry. The processing circuitry can include devices such as an application-specific integrated circuit (ASIC), configurable logic devices (e.g., simple programmable logic devices (SPLDs), complex programmable logic devices (CPLDs), and field programmable gate arrays (FPGAs), and other circuit components that are arranged to perform the functions recited in the present disclosure.

The processor 142 executes one or more sequences of one or more instructions contained in the program code structures 144 and 150. Alternatively, the instructions can be read from another computer-readable medium, such as a hard disk or a removable media drive. One or more processors in a multi-processing arrangement can also be employed to execute the sequences of instructions contained in the program code structures 144 and 150. In alternative embodiments, hard-wired circuitry can be used in place of or in combination with software instructions. Thus, the disclosed embodiments are not limited to any specific combination of hardware circuitry and software.

Additionally, the term "computer-readable medium" as used herein refers to any non-transitory medium that participates in providing instructions to the processor 142 for execution. A computer readable medium can take many forms, including, but not limited to, non-volatile media or volatile media. Non-volatile media includes, for example, optical, magnetic disks, and magneto-optical disks, or a removable media drive. Volatile media includes dynamic memory.

Also illustrated in FIG. 4 is a generalized depiction of an MRI system program storage (memory) 150, where stored program code structures are stored in non-transitory computer-readable storage media accessible to the various data processing components of the MRI system 100. As those in the art will appreciate, the program store 150 can be segmented and directly connected, at least in part, to different ones of the system 103 processing computers having most immediate need for such stored program code structures in their normal operation (i.e., rather than being commonly stored and connected directly to the MRI system controller 130).

Additionally, the MRI system 100 as depicted in FIG. 4 can be utilized to practice exemplary embodiments described herein below. The system components can be divided into different logical collections of "boxes" and typically comprise numerous digital signal processors (DSP), microprocessors and special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Furthermore, not only does the physical state of the processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an image reconstruction process and/or sometimes an image reconstruction map (e.g., coil sensitivity map, unfolding map, ghosting map, a distortion map etc.) generation process, an array of computer-readable accessible data value storage sites in physical storage media will be transformed from some prior state (e.g., all uniform "zero" values or all "one" values) to a new state wherein the physical states at the physical sites of such an array vary between minimum and maximum values to represent real world physical events and conditions (e.g., the internal physical structures of a patient over an imaging volume space). As those in the art will appreciate, such arrays of stored data values represent and also constitute a physical structure, as does a particular structure of computer control program codes that, when sequentially loaded into instruction registers and executed by one or more CPUs of the MRI system 100, causes a particular sequence of operational states to occur and be transitioned through within the MRI system 100.

MRI images are formed by acquiring NMR (nuclear magnetic resonance) RF response signals (e.g. echo data) spatially encoded for respectively corresponding points in k-space. The RF response values are typically generated by "traversing" k-space in two or three dimensions according to a configured MRI pulse sequence. The acquisition of data in the frequency-encoded direction (e.g., along the x-axis) is typically rapid and on the order of several milliseconds. However, along the phase-encoded axis (e.g., y-axis), a different value of the applied phase-encoding gradient is used to sample each point. Therefore, the acquisition time for an MRI image can be largely determined by the number of phase-encoding steps.

While certain implementations have been described, these implementations have been presented by way of example only, and are not intended to limit the teachings of this disclosure. Indeed, the novel methods, apparatuses and systems described herein can be embodied in a variety of other forms; furthermore, various omissions, substitutions and changes in the form of the methods, apparatuses and systems described herein can be made without departing from the spirit of this disclosure.

The invention claimed is:

1. An imaging apparatus, comprising:
   processing circuitry configured to
      obtain magnetic resonance imaging (MRI) data, the MRI data including imaging segments and corresponding navigator segments, each imaging segment sampled over a respective regions of two or more regions of a k-space grid, one of the navigator segments being selected as a reference navigator segment;
      generate, for each imaging segment of the imaging segments, a respective phase map based on the reference navigator segment and a corresponding navigator segment of the each imaging segment;
      apply the respective phase maps to the corresponding imaging segments to generate corrected imaging segments;
      average the corrected imaging segments in k-space to generate averaged imaging segments; and
      reconstruct an MRI image based on the averaged imaging segments.

2. The apparatus according to claim 1, wherein the processing circuitry is further configured to obtain the MRI data, wherein a number of imaging segments is greater than a number of the two or more regions in the k-space grid.

3. The apparatus according to claim 1, wherein the processing circuitry is further configured to obtain the MRI data, wherein more of the imaging segments are sampled at a central region of the k-space grid than are sampled at a peripheral region of the k-space grid, the central region of the k-space grid including lower spatial frequencies than the peripheral region.

4. The apparatus according to claim 3, wherein the processing circuitry is further configured to obtain the MRI data, wherein a predetermined number of the imaging segments sampled over the at least one substantially central segment of the k-space grid is rejected.

5. The apparatus according to claim 1, wherein the processing circuitry is further configured to generate the respective phase map, wherein the respective phase map corresponding to one of the imaging segments is a phase of a product of a navigator segment image of the navigator segments corresponding to the one of the imaging segments and a conjugate of a reference navigator image of the reference navigator segment.

6. The apparatus according to claim 1, wherein the processing circuitry is further configured to reconstruct the MRI image, wherein the MRI image is reconstructed by an inverse Fourier Transform of the averaged imaging segments.

7. The apparatus according to claim 1, wherein the processing circuitry is further configured to apply the respective phase map to the corresponding imaging segments by convolving, in the k-space, the respective imaging segments with the corresponding phase maps.

8. The apparatus according to claim 1, wherein the processing circuitry is further configured to obtain the MRI data, wherein the imaging segments includes a third imaging segment that spans a boundary in the k-space between a first imaging segment and a second imaging segment that are sampled in adjacent regions of the k-space.

9. A method for non-uniform k-space sampling, comprising:
obtaining magnetic resonance imaging (MRI) data, the MRI data including imaging segments and corresponding navigator segments, each imaging segment sampled over a respective regions of two or more regions of a k-space grid, one of the navigator segments being selected as a reference navigator segment;
generating, for each imaging segment of the imaging segments, a respective phase map based on the reference navigator segment and a corresponding navigator segment of the each imaging segment;
applying the respective phase maps to the corresponding imaging segments to generate corrected imaging segments;
averaging the corrected imaging segments in k-space to generate averaged imaging segments; and
reconstructing an MRI image based on the averaged imaging segments.

10. The method according to claim 9, wherein a number of imaging segments is greater than a number of the two or more regions in the k-space grid.

11. The method according to claim 9, wherein more of the imaging segments are sampled at a central region of the k-space grid than are sampled at a peripheral region of the k-space grid, the central region of the k-space grid including lower spatial frequencies than the peripheral region.

12. The method according to claim 11, wherein a predetermined number of the imaging segments sampled over the at least one substantially central segment of the k-space grid is rejected.

13. The method according to claim 9, wherein the respective phase map corresponding to one of the imaging segments is a phase of a product of a navigator segment image of the navigator segments corresponding to the one of the imaging segments and a conjugate of a reference navigator image of the reference navigator segment.

14. The method according to claim 9, wherein the MRI image is reconstructed by an inverse Fourier Transform of the averaged imaging segments.

15. The method according to claim 9, wherein the processing circuitry is further configured to apply the respective phase map to the corresponding imaging segments by convolving, in the k-space, the respective imaging segments with the corresponding phase maps.

16. The method according to claim 9, wherein the processing circuitry is further configured to obtain the MRI data, wherein the imaging segments includes a third imaging segment that spans a boundary in the k-space between a first imaging segment and a second imaging segment that are sampled in adjacent regions of the k-space.

17. A non-transitory computer readable storage medium including executable instructions, wherein the instructions, when executed by circuitry, cause the circuitry to perform the method according to claim 9.

* * * * *